(12) United States Patent
Hacker (10) Patent No.: US 11,364,371 B1
(45) Date of Patent: Jun. 21, 2022

(54) SAFETY SYRINGE EXTENSION ADAPTER HAVING PIVOTABLE APPLICATOR UNIT AND OPTIONAL WIPER GUARD

(71) Applicant: Nano 2.0 Business Press, LLC, Delray Beach, FL (US)

(72) Inventor: Steven M. Hacker, Delray Beach, FL (US)

(73) Assignee: Nano Surgical, LLC, Delray Beach, FL (US)

( * ) Notice: Subject to any disclaimer, the term of this patent is extended or adjusted under 35 U.S.C. 154(b) by 535 days.

(21) Appl. No.: 16/578,382

(22) Filed: Sep. 22, 2019

(51) Int. Cl.
*A61M 35/00* (2006.01)
*A61M 39/10* (2006.01)

(52) U.S. Cl.
CPC ...... *A61M 35/003* (2013.01); *A61M 39/1011* (2013.01); *A61M 39/1055* (2013.01); *A61M 2039/1077* (2013.01)

(58) Field of Classification Search
CPC ............ A61M 35/003; A61M 39/1011; A61M 39/1055; A61M 2039/1077; A61M 35/00; A61M 39/10; A61M 39/00; A61M 39/105; A61M 5/178
See application file for complete search history.

(56) References Cited

U.S. PATENT DOCUMENTS

2010/0043242 A1\* 2/2010 Stevens ................. B26B 21/521
30/527
2018/0326163 A1\* 11/2018 Bailey ................... A61M 5/425

\* cited by examiner

*Primary Examiner* — Jason E Flick
(74) *Attorney, Agent, or Firm* — Nancy J. Flint, Attorney At Law, P.A.; Nancy J. Flint, Esq.

(57) ABSTRACT

A safety syringe extension adapter and an applicator unit having at least one applicator is disclosed. More particularly, an applicator unit is connected to a syringe by a safety syringe extension adapter and including an applicator wherein the applicator unit comprises pivotal movement relative thereto about two separate pivot axes for following the skin contours of a user during certain skin related procedures such as applying Platelet Rich Plasma (PRP) to the skin; applying a chemical peel to the skin using Trichloracetic Acid (TCA), glycolic acid (GA), or any fluid for purposes of applying to the skin; applying antiseptics to sterilize the skin prior to or after a procedure; or applying analgesics to the skin surface or any other fluid to the skin surface.

11 Claims, 11 Drawing Sheets

SAFETY SYRINGE EXTENSION ADAPTER HAVING PIVOTABLE APPLICATOR UNIT AND OPTIONAL WIPER GUARD

FIELD OF THE INVENTION

The invention relates to a method and device for moving fluid from a syringe to a skin surface using safety syringe extension adapters with applicator units having at least one applicator. More particularly, the invention relates to an applicator unit being connected to a syringe by a safety syringe extension adapter and including an applicator wherein the applicator unit comprises pivotal movement relative thereto about two separate pivot axes for following the skin contours of a user during certain skin related procedures such as applying Platelet Rich Plasma (PRP) to the skin; applying a chemical peel to the skin using Trichloracetic Acid (TCA), glycolic acid (GA), or any fluid for purposes of applying to the skin; applying antiseptics to sterilize the skin prior to or after a procedure; or applying analgesics to the skin surface or any other fluid to the skin surface.

BACKGROUND OF THE INVENTION

It is conventional for dermatologists and plastic surgeons to apply a peel, or PRP to the skin. Several methods are used for these procedures including large cotton swabs, gauze, foam materials, or injection through an uncovered syringe. If using a syringe, typically much of the PRP or the TCA, for example, or other fluid, is lost as it is pushed through the syringe distal opening and spills over the face where it can get in the eyes, or mucous membranes, which is dangerous and can be harmful to the patient. Additionally, much of the valuable fluid can be lost as waste. Alternatively, if using cotton swab or other materials such as gauze or foam pads, much of the fluid, i.e. TCA or PRP, are absorbed by the applicators and/or are not evenly applied on the skin, resulting in wasted fluid and uneven application. The ability to have a skin applicator that doesn't waste fluid, doesn't spill unnecessarily into eyes or mucous membranes, provides for pivotal movement, provides conformance with the skin allowing the applicator unit to easily follow the skin contours of a user during applying fluid to skin and attaches simply to a syringe or any vial containing the fluid. There is a need, to create an applicator, that conforms to the skin surface by pivoting about two axes, the parallel axes that is parallel to applicator and another axis that is substantially perpendicular to the applicator.

U.S. Patent Pubin. No. 2018/0043145 A1 discloses an applicator for topical application of a liquid. The applicator comprises in one embodiment a container containing comprising an opening in fluid contact with a nib for a controlled release of a acidic liquid, wherein the nib comprises a plurality of fibers and an adhesive material adhering the fibers. The nib is a part which may come into contact with an area to be treated, such as tissue, mucus membrane, nail, etc., in order to deliver a dose of an active ingredient.

WO 2018/087140 A1 discloses an applicator device comprising an applicator tip and a container part. The container part comprises: (i) a container comprising a container wall, a valve, and a plunger, wherein the container wall, the valve, and the plunger together define a variable storage volume, especially for containing a liquid, wherein the plunger comprises a circumferential wall, sealingly contacting the container wall; and (ii) a plunger advance system functionally coupled to the plunger and configured to advance the plunger for reducing the storage volume for expelling at least part of the liquid via said valve to said tip, wherein the plunger advance system is arranged outside the storage volume.

U.S. Pat. No. 9,844,654 discloses a fluid applicator apparatus. In one embodiment, the main body of the apparatus has an opener element positioned within the interior of the main body at the main body mid portion. In one embodiment, the opener element is a protuberance that is configured to actuate (e.g., open) (e.g., insert into) an operable door within a fluid housing. In one embodiment, the opener element is triangular in shape and rigidly positioned within the interior of the main body at the main body mid portion. In one embodiment, the opener element has a pointed front end angled acutely so as to facilitate the actuating (e.g., opening) of an operable door (e.g., a fluid housing operable door), a top end shaped to facilitate the retention of such an operable door in an open position, and a back end. In one embodiment, the top end is more acutely angled in comparison to the pointed front end thereby facilitating positioning of an opened fluid housing operable door on such top end (so as to retain the opened operable door in an open position). In one embodiment, the width of the opener element is sufficiently narrow so as to retain a hollow passage within the interior of the main body. In one embodiment, the width of the opener element is sufficiently narrow so as to facilitate (e.g., not hinder) the passage of a fluid through the interior of the main body to the applicator.

U.S. Pat. No. 4,220,151 discloses a disposable Luer lock syringe with an integral Luer tapered needle connector and an integral, internally threaded, Luer lock retaining collar surrounding the connector and having a plurality of circumferentially spaced, longitudinal grooves. The grooved collar is circumferentially continuous and has sufficient rigidity for obtaining a desired fluid-tight connection with the hub of a needle assembly, while the grooves provide the collar with sufficient flexibility to permit the fracturing of the connector after the syringe is used so as to prevent reuse of the syringe.

U.S. Pat. No. 8,105,312 discloses a syringe connectable to a port in a fixed manner as well as capable of demonstrating high operational performance even in the case of direct connection where a connector is not used; a connector used for the syringe; and a syringe able to attach the connector thereto. The medical syringe includes a cylindrical connection supporting member which enhances the holding force of a luer part inserted into a port when the medical syringe is connected to the port. The connection supporting member is set by sliding along the luer or a syringe body in a state of being movable between a first position near a tip of the luer and a second position away from the tip of the luer. The medical syringe is characterized in that, when the connection supporting member is moved to the second position, the tip of the luer part is exposed.

U.S. Patent Publn. No. US2010/0043242 discloses a safety razor having a blade unit and at least one blade and a handle casing. A pivotal connection structure is disposed between the blade unit and the handle casing. A first member is connected to the blade unit and a second member is connected to the handle casing. A joint member connects the first member and the second member and facilitates movement of the first member relative to the second member about a hinge axis that is substantially perpendicular to the at least one blade.

U.S. Pat. No. 6,615,498 discloses a razor assembly having a razor cartridge designed for pivotal, swivel and torsional movement during shaving includes a handle and a flexible member having a first end connected to the handle at a pivot axis, a second free end extending beyond the handle and a longitudinal axis extending through the first and second ends of the flexible member. The razor cartridge, which has a major axis and one or more razor blades, is pivotally connected to the second free end of the flexible member for pivoting about an axis that is substantially parallel to the major axis of the razor cartridge. In addition, the second free end of the flexible member, and the razor cartridge pivotally connected thereto, are movable along an arcuate path centered at the pivot axis and are rotatable about an axis substantially parallel to the longitudinal axis of the flexible member.

U.S. Pat. No. 7,197,825 discloses a shaving blade unit including a plastic housing having a front portion and a rear portion and two side surfaces extending from the front portion to the rear portion. The housing has a length extending from one side surface to the other side surface. Positioned between the front and rear surface of the housing are one or more shaving blades having a blade length extending along respective one or more parallel blade axes. A guard at the front portion of the housing includes an elastomeric member that extends along a guard axis that is parallel to the respective one or more blade axes. The elastomeric member has a length along the guard axis that is greater than or equal to the blade length.

U.S. Pat. No. 5,787,586 discloses a shaving system including a replaceable shaving cartridge and a shaving razor handle. The replaceable shaving cartridge has a housing carrying blades, a guard and a cam surface. The cartridge includes an interconnect member having a pivotal support structure that pivotally supports the housing and a base structure adapted to be removably and fixedly attached to the handle. A shaving razor handle has an elongated hand gripping structure and a cartridge support structure extending from an end of the hand gripping structure. The cartridge support structure has an extension with outer side surfaces that mate with inwardly directed surfaces of a recess on the cartridge and an end surface with an opening. The extension has an asymmetrical shape to ensure proper orientation. A spring-biased plunger is retained in the cartridge support structure and extends through the opening of the cartridge support structure.

U.S. Pat. No. 5,953,824 discloses razors adapted to support a razor head during shaving while permitting the razor head to move relative to the razor in response to forces encountered during shaving. The razor head can swivel and pivot about an axis normal to a central axis of the razor and normal to an imaginary axis defined by the points of attachment of the razor to a razor head. An engagement arm comprises a slot for controlling the movement of the engagement during shaving, as well as during loading/unloading of a razor head. The razor head can maintain shave relation with the skin regardless of the angular differences between the cartridge head, razor handle/grip and shaving motion during shaving.

SUMMARY OF THE INVENTION

The invention relates to a method and device for moving fluid from a syringe to a skin surface using a safety syringe extension adapter having an applicator unit capable of independent pivotal movement about two separate pivot axes. In one embodiment, the applicator unit comprises a wiper guard to absorb fluid so it does not run down the face or other body part of a person to whom the fluid is being applied.

In one embodiment, the safety syringe extension adapter includes an applicator unit having at least one applicator, a tube, and a pivotal connection structure disposed between the applicator unit and the tube, and further comprising an adapter attached to a syringe via methods well known in the prior art such as a Luer lock, or by other methods now known or later developed. The syringe contains a fluid to be topically applied to the skin. The applicator unit is connected to the tube via a pivotal connection structure allowing for independent pivotal movement relative thereto about two separate pivot axes which for following the skin contours of a user during applying fluid to skin.

In one embodiment, the safety syringe extension adapter comprises a wiper guard made of an absorbable material and attached to the applicator unit.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings.

DETAILED DESCRIPTION OF THE INVENTION

Herein, "proximal" means closest to the surgeon's hand and "distal" means furthest away from surgeon's hand or closest to the skin surface. Also, "connected" encompasses configurations in which one element is directly secured or mounted to another element by affixing the element directly to the other element; configurations in which the element is indirectly secured or mounted to the other element by affixing the element to an intermediate member which is affixed to the other element; and configurations in which one element is integral with another element, i.e., one element is essentially part of the other element.

Herein, "joint" encompasses configurations in which one element is directly secured or mounted to another element by affixing the element directly to the other element; and configurations in which one element is integral with another element, i.e., one element is essentially part of the other element.

Figure 1:
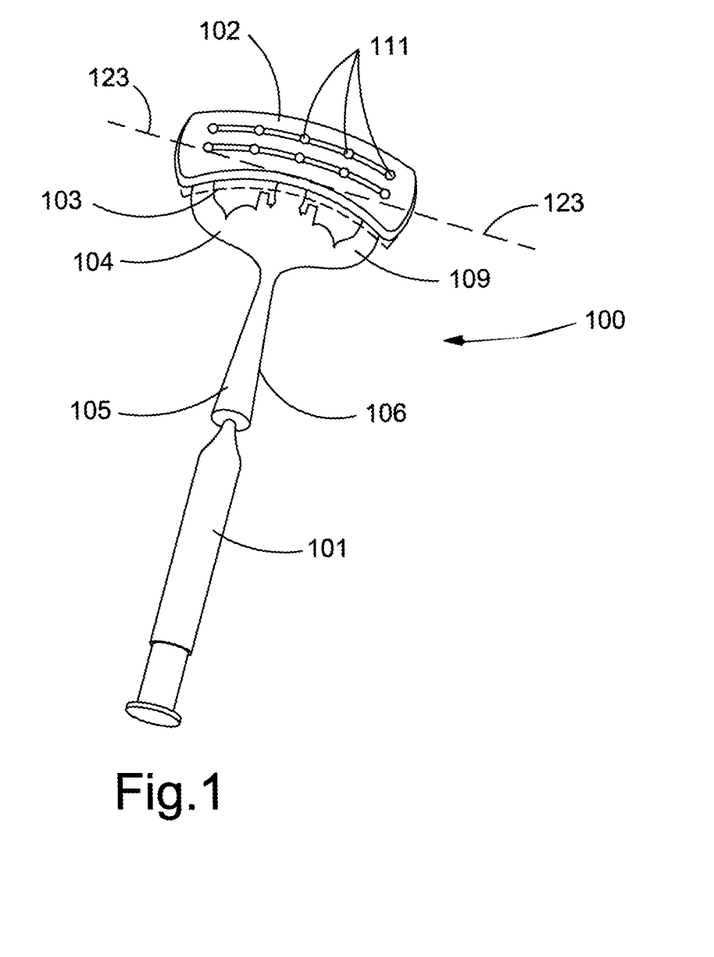
FIG. 1 is a perspective view of a safety syringe extension adapter according to one embodiment of the invention.

FIG. 1 is a perspective view of safety syringe extension adapter 100 attached to syringe 101 according to one embodiment of the invention. Safety syringe extension adapter 100 comprises applicator unit 102 which comprises pivotal connection structure (not shown), connecting member 104 and wiper guard 103. Applicator unit 102 comprises a hollow interior. Tube unit 105 comprises an outer tube casing 106 which defines an inner tube reservoir (not shown). Applicator unit 102 further comprises a plurality of applicator openings 111 disposed in a lateral arrangement on upper surface of applicator unit 102. Safety syringe extension adapter 100 is connected to syringe 101 at proximal end of tube unit 105. Syringe 101 can be attached to tube unit 105 by any means of connection now known or later developed such as Luer locks or threads. Applicator unit 102 comprises a plastic, soft rubber or elastic material that is pliable and conforms to the shape of skin upon the application of external pressure. Applicator unit 102 is pivotally connected to connecting member 104 and pivotal connection structure, allowing for pivoting of applicator unit 102 about perpendicular pivot axis 123, which axis is disposed in a substantially perpendicular direction to the lateral arrangement of applicator openings 111.

Figure 2:
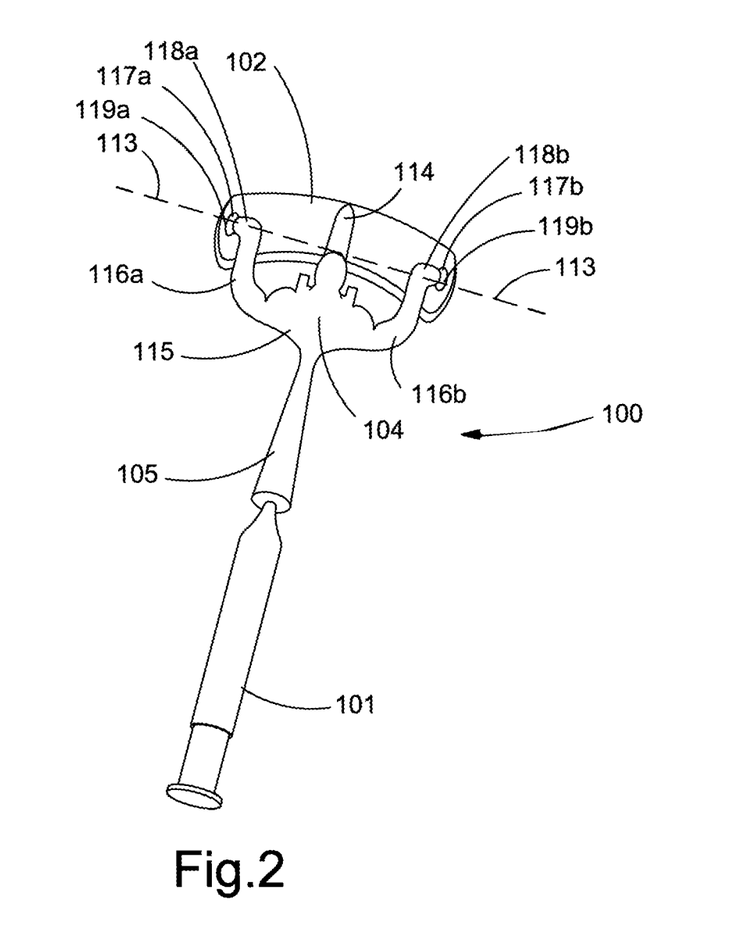
FIG. 2 is a rear view of the applicator unit shown in FIG. 1.

FIG. 2 is a rear view of safety syringe extension adapter 100 shown in FIG. 1. Applicator unit 102 comprises connecting member 104 and pivotal connection structure (not shown) allowing for pivoting of applicator unit 102 about parallel pivot axis 113, which axis is disposed in a substantially parallel direction to the lateral arrangement of applicator openings 111. Centrally placed cam surface 114 is disposed on the back side of applicator unit 102. Connecting member 104 comprises body 115 and pair of arms 116a, 116b extending at a distal position outwardly from body 115. Each of arms 116a, 116b comprises a finger 118a, 118b which pivotally connects to applicator unit 102 by insertion into pivot bearings (not shown), allowing applicator unit 102 to pivot about parallel pivot axis 113. Arms 116a, 116b also each comprise a distal opening 117a, 117b disposed in the vicinity of the ends of fingers 118a, 118b. Each distal opening 117a, 117b communicates with apertures 119a, 119b disposed on each outer side of applicator unit 102.

Figure 3:
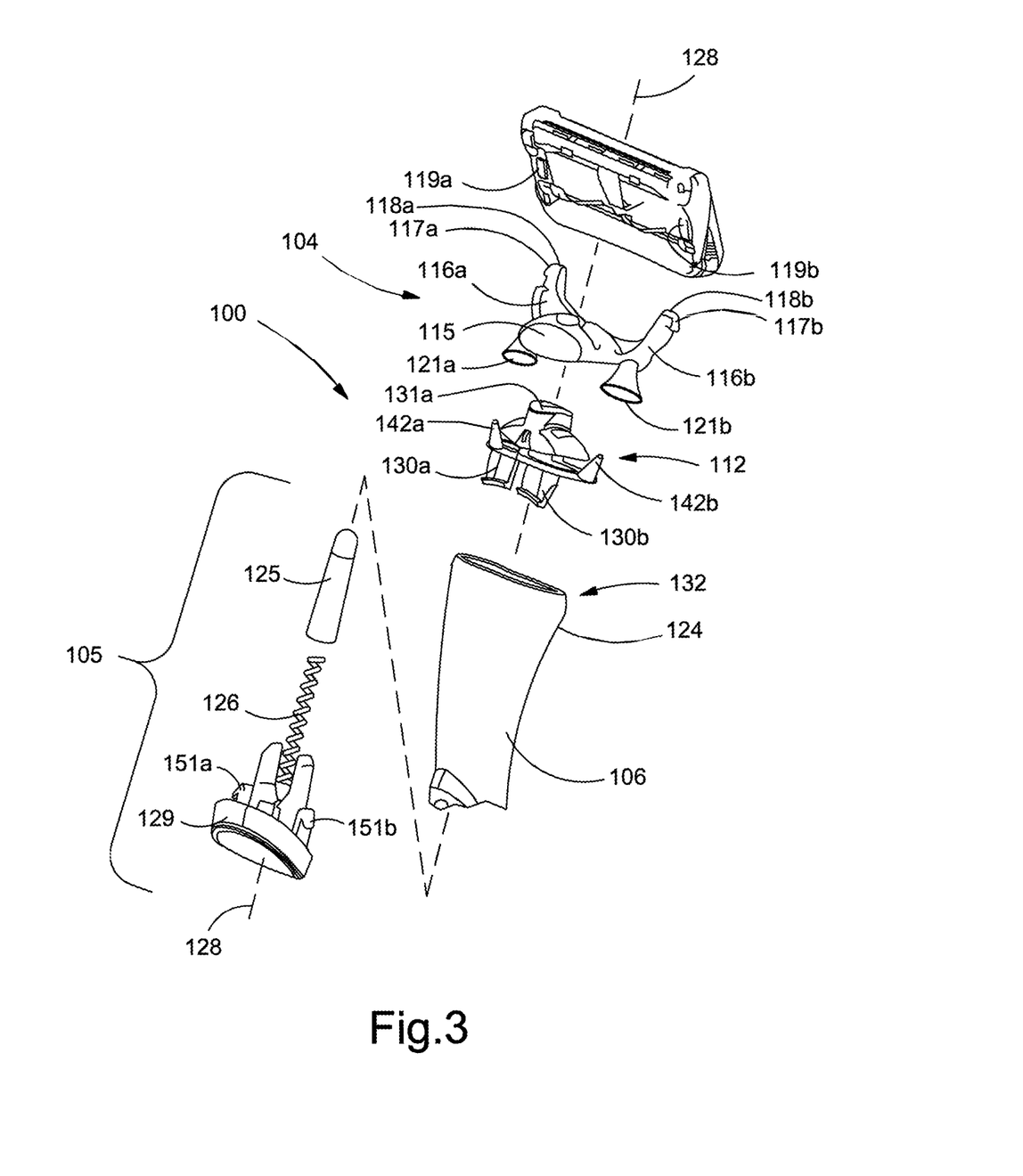
FIG. 3 is an exploded perspective view of a subassembly of the safety syringe extension adapter shown in FIG. 1.

FIG. 3 is an exploded view of safety syringe extension adapter 100 shown in FIG. 1. Pivotal connection structure 112 is disposed between connecting member 104 and distal end of tube unit 105 at tube end 124 which is sized to mate with pivotal connection structure 112. Tube unit 105 further comprises spring-biased plunger 125 and spring 126. Pivotal connection structure 112, spring-biased plunger 125, spring 126 and ring-shaped plunger-spring assembly collar 129 are disposed along a common longitudinal central axis 128. Ring-shaped plunger-spring assembly collar 129 comprises an inner cavity having a diameter smaller than the diameter of tube end 124. A pair of latch arms 151a, 151b are disposed on the distal top surface of ring-shaped plunger-spring assembly collar 129 which secure base of spring-biased plunger 125. Pivotal connection structure 112 further comprises a pair of latch arms 130a, 130b that help secure pivotal connection structure 112 to tube unit 105. Distal end of tube unit 105 comprises tube end 124 having slot 132 through which distal end of spring-biased plunger 125 can pass. Pivotal connection structure 112 further comprises conduits 142a and 142b that on proximal ends communicate with reservoir 110 of tube unit 105 through slot 132 and on distal ends communicate with funnel shaped projections 121a and 121b disposed on the proximal side of connecting member 104.

To assemble connecting member 104 and pivotal connection structure 112 with tube unit 105, first an assembly comprising spring 126, spring-biased plunger 125 and ring-shaped plunger-spring assembly collar 129 is formed by inserting spring 126 into an internal cavity of spring-biased plunger 125. Spring 126 may be placed over a cylindrical extension (not shown) to maintain its position within the interior of spring-biased plunger 125. Spring 126 is maintained in removable communication with ring-shaped plunger-spring assembly collar 129 by any means now known or later developed. In one embodiment, spring 126 is inserted over a nib (not shown) that maintains communication with ring-shaped plunger-spring assembly collar. The assembly comprising spring 126, spring-biased plunger 125 and ring-shaped plunger-spring assembly collar 129 is inserted into tube end 124 wherein latch arms 129a and 129b engage a lip formed in the distal end of tube end 124, thus securing connection of the assembly with tube end 124. The assembly comprising spring 126, spring-biased plunger 125 and ring-shaped plunger-spring assembly collar 129 is inserted through slot 132 at tube end 124 into the interior cavity 110 of tube unit 105. Next, tube unit 105 is placed against the proximal portion of pivotal connection structure 112, wherein distal end of spring-biased plunger 125 passes through pivotal connection structure slot 131a and thereafter through connecting member slot 131b.

Also shown are body 115 of connecting member 104 and pair of arms 116a, 116b extending at a distal position outwardly from body 115. Each of arms 116a, 116b comprises a finger 118a, 118b which pivotally connects to applicator unit 102 by insertion into pivot bearings (not shown), allowing applicator unit 102 to pivot about parallel pivot axis 113. Arms 116a, 116b also each comprise a distal opening 117a, 117b disposed in the vicinity of the ends of fingers 118a, 118b. Each distal opening 117a, 117b communicates with apertures 119a, 119b disposed on each outer side of applicator unit 102.

Figure 4A:
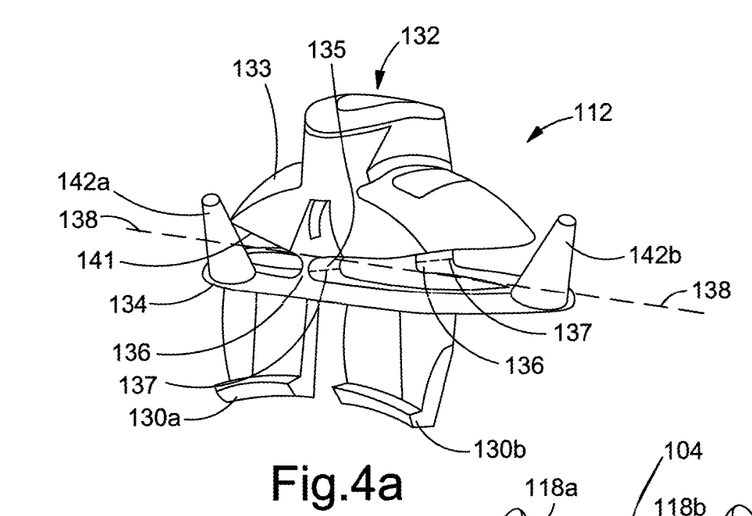
FIGS. 4A, 4B and 4C are perspective views of the pivotal connection structure shown in FIG. 3.

FIG. 4A is a perspective view of pivotal connection structure 112 shown in FIG. 3. Referring to FIG. 4A, pivotal connection structure 112 comprises first member 133 which connects to connecting member 104 (see FIG. 4C) and second member 134 which connects to tube end 124 (not shown). Each of first member 133 and second member 134 has a first joint portion 135 and second joint portion 136, respectively. Pivotal connection structure 112 further includes joint member 137 (see FIGS. 4A and 4B) for joining, in a hinged manner, first joint portion 135 of first member 133 with second joint portion 136 of second member 134.

As used herein, "in a hinged manner" means that two separate members are joined by a third member wherein the two separate members are movable about a pivot axis which passes through the third member. This pivot axis is also called "hinge axis."

Pivotal connection structure 112 is constructed such that joint member 137 comprises a hinge axis 138 disposed between first joint portion 135 of first member 133 and second joint portion 136 of second member 134, which operates as perpendicular pivot axis 123 shown in FIG. 1. Joint member 137 can be formed by (or, include) either a single joint element or a plurality of (e.g., two or more) separated joint elements which is (or are) disposed along hinge axis 138 or perpendicular pivot axis 123. Such a plurality of separated joint elements can be formed by either an identical material or different materials on each element.

Joint member 137 may have a thinner wall section toward hinge axis 138 than toward at least one of first joint portion 135 and second joint portion 136 of first member 133 and second member 134 to facilitate movement of first member 133 relative to second member 134 about a single axis (e.g., hinge axis 138). In certain embodiments, joint member 137 may have a thinner wall section toward hinge axis 138 than toward either of first joint portion 135 and second joint portion 136 of first member 133 and second member 134 (e.g., a living hinge). The thinner wall section toward the center of joint member 137 may allow for a more precise and controllable location of hinge axis 138. For example, if joint member 137 has a uniform wall section, the location of hinge axis 138 may vary significantly between first joint portion 135 and second joint portion 136. Joint member 137 may be concave or have a radius to facilitate repeated flexing of the joint member 137 without cracking or breaking.

In the embodiment shown in FIG. 4A, joint member 137 (as a whole) has an elongated shape such that it constitutes hinge axis 138 disposed between first joint portion 135 and second joint portion 136 of first member 133 and second member 134. Joint member 137 includes first joint portion 135 and second joint portion 136 which are disposed along hinge axis 138. First joint portion 135 and second joint portion 136 constitute joint member 137. Hinge axis 138 coincides with perpendicular pivot axis 123 shown in FIG. 1. In order to constitute pivotal connection structure 112 for pivotal movement about perpendicular pivot axis 123, it should be noted that first member 133 and second member 134 are joined only by first joint portion 135, joint member 137 and second joint portion 136 in the embodiment shown. In other words, there is no other element(s) which joints or connects first member 133 to second member 134 other than first joint portion 135 and second joint portion 136.

In an alternative embodiment, joint member 137 can be formed by a unitary material (i.e., one elongated element, instead of two or more separated joint elements disposed along the hinge axis.)

In one embodiment, at least one of first member 133 and second member 134 has a convexly curved face facing the other of the first member 133 or second member 134. In the embodiment shown in FIG. 4A, first member 133 has a convexly curved face 141 facing second member 134. The formation of convexly curved face 141 at first member 133 can facilitate a wider range of pivotal movement at pivotal connection structure 112.

Figure 4B:
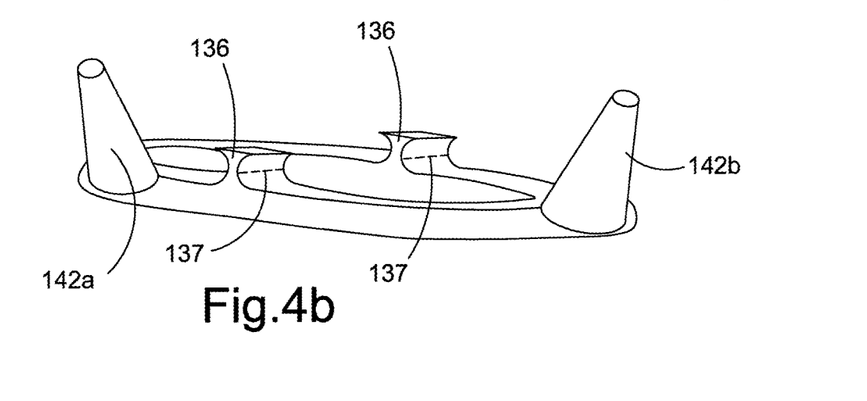
Figure 4C:
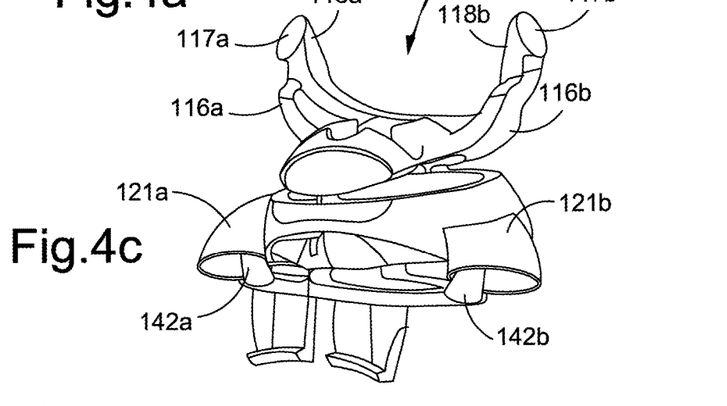

As seen in FIGS. 4A, 4B and 4C, conduit projections 142a, 142b are disposed on the distal surface and at the most peripheral outer aspect of pivotal connection structure 112 which have open communication through to the proximal surface of pivotal connection structure 112. Conduit projections 142a, 142b are disposed peripheral to the outer edges of first member 133 so as not to interfere with pivotability of applicator unit 102 about parallel pivot axis 113. Conduit projections 142a, 142b are in communication and mate with funnel shaped projections 121a, 121b disposed on the proximal side of connecting member 104.

Figure 5:
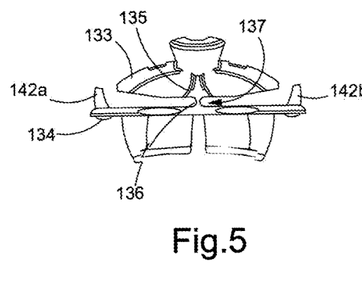
FIG. 5 is a front view of the pivotal connection structure shown in FIG. 3.
Figure 6:
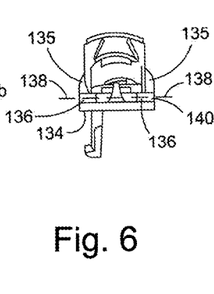
FIG. 6 is a side view of the pivotal connection structure shown in FIG. 3.
Figure 7:
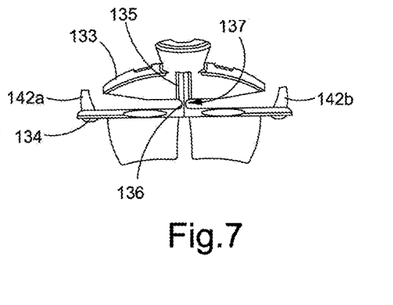
FIG. 7 is a rear view of the pivotal connection structure shown in FIG. 3.

FIGS. 5, 6 and 7 are front, side and rear views of pivotal connection structure 112 shown in FIG. 3, respectively. Pivotal connection structure 112 includes first member 133, second member 134, and joint member 137. Hinge axis 138 is disposed between first joint portion 135 and second joint portion 136 of first member 133 and second member 134. In this embodiment, joint member 137 has first joint element 135 and second joint element 136 disposed along hinge axis 138 as shown in FIG. 6. Pivotal connection structure 112 comprises conduit projections 142a and 142b on peripheral outer edges of first member 133 that on proximal ends communicate with reservoir 110 of tube unit 105 through slot 132 and on distal ends communicate with funnel shaped projections 121a and 121b disposed on the proximal ends of arms 116a, 116b.

Since pivotal connection structure 112 allows for a pivotal movement about perpendicular pivot axis 123 by a simple structure, safety syringe extension adapter 100 can be produced by a simple manufacturing process.

Joint member 137 (e.g., formed by first joint element 135 and second joint element 136) comprises a resilient material such as a thermoplastic material, a rubber material, a metal material, or the like. Applicable thermoplastic materials for joint member 137 include, but not are limited to, polyamide (nylon); polypropylene; polyester; polyethylene; and styrene ethylene butylene styrene (SEBS).

In one embodiment, first member 133, second member 134 and joint member 137 may be formed from the same material. In one embodiment, first member 133, second member 134 and joint member 137 may be formed from a thermoplastic material. It is understood that other thermoplastic materials may also be used, including, but not limited to nylon, polyethylene, and polypropylene, and acrylonitrile butadiene styrene (ABS). The thermoplastic material of joint member 137 may provide sufficient flexibility for pivoting while preventing fatigue or premature failure of joint member 137 over numerous cycles of pivoting about hinge axis 64.

Alternatively, first member 133, second member 134, and joint member 137 may be formed by at least two different materials. In one embodiment, first member 133 and second member 134 may be formed from the same material, while joint member 137 may be formed from a different material. For example, first member 133 and second member 134 may be formed from a thermoplastic material (e.g., polyoxymethylene (POM) copolymer), while joint member 137 may be formed from an adhesive material. Examples of suitable adhesive materials include but are not limited to a polyurethane adhesive and a methacrylate adhesive.

In one embodiment, first member 133, second member 134 and joint member 137 can be formed from the same material by using an injection molding process of a thermoplastic material. In this embodiment, since pivotal connection structure 112 can be formed by injection molding, safety syringe extension adapter 100 can be produced by a simple manufacturing process.

If desired, first member 133, second member 134, and joint member 137 can be formed by three different materials.

The elastic property of the joint member 137 can vary depending on the material employed and the thickness of the joint member 137. In one embodiment, the resilient material for the joint member 137 may be a polyoxymethylene (POM) copolymer.

Figure 8:
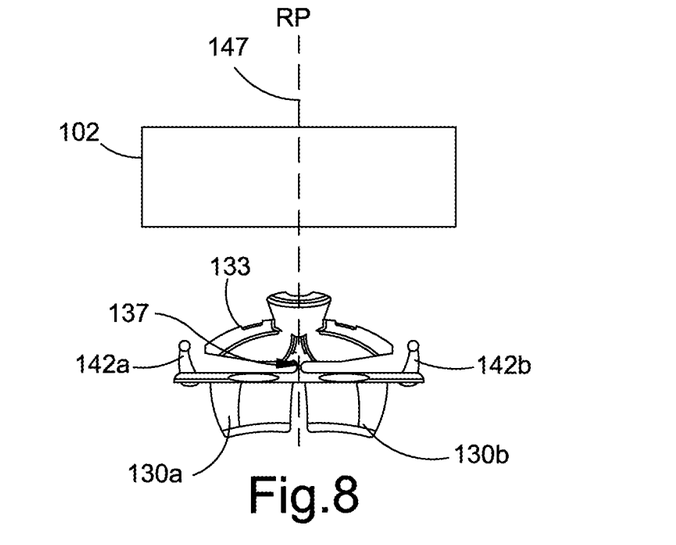
FIGS. 8 and 9 are schematic drawings of the pivotal connection structure shown in FIG. 3.
Figure 9:
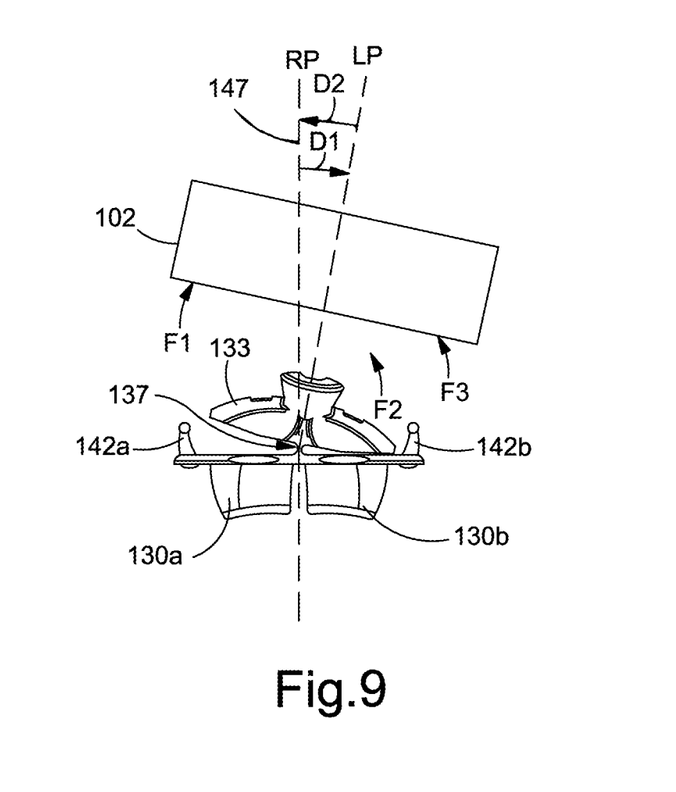

FIGS. 8 and 9 are schematic drawings illustrating the relative movements between applicator unit 102 and pivotal connection structure 112 when applicator unit 102 pivots about perpendicular pivot axis 123. Applicator unit 102 begins at rest position RP about first pivot axis 147, which is perpendicular to perpendicular pivot axis 123.

In FIG. 8, when no force is applied, applicator unit 102 is in rest position RP and first pivot axis 147 is also in rest position RP. In this state, applicator unit 102 is ready to be biased by a return force generated by pivotal connection structure 112 (more specifically, joint member 137) when it pivots about perpendicular pivot axis 123 away from rest position RP.

In FIG. 9, upon application of force F1, applicator unit 102 leans in direction D1 to reach lean position LP as indicated by moved pivot axis 148. This lean causes a strain at joint member 137 of pivotal connection structure 112. In response to the strain (and due to the resilient nature of joint member 33), joint member 137 of pivotal connection structure 112 generates a reverse force F2 which is applied to first member 133. Reverse force F2 is transmitted to applicator unit 102 through first member 133 as a return force F3 in the direction D2. Return force F3 pushes applicator unit 102 back to rest position RP.

Similarly, applicator unit 102 and joint member 137 of pivotal connection structure 112 work similarly when a force opposite to force F1 is applied to applicator unit 102.

In one embodiment, applicator unit 102 has a pivot range (about perpendicular pivot axis 123) up to about 15° in either direction from rest position RP. Other pivot ranges both larger and smaller may be used as desired.

Figure 10:
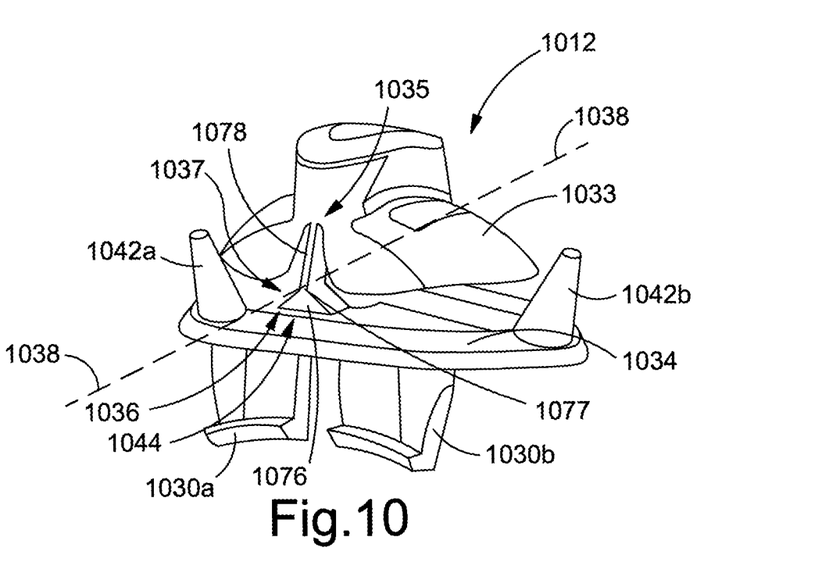
FIG. 10 is a perspective view of a pivotal connection structure according to one embodiment of the invention.
Figure 11:
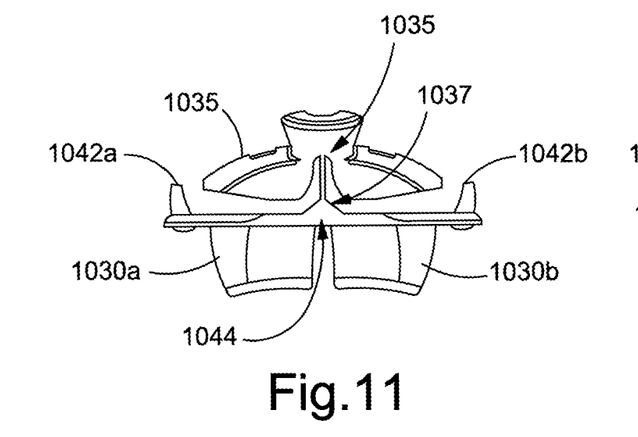
FIG. 11 is a front view of the pivotal connection structure shown in FIG. 10.
Figure 12:
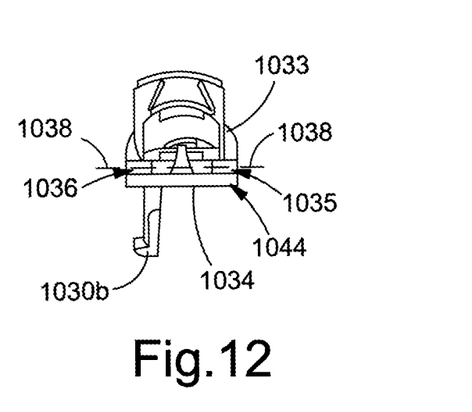
FIG. 12 is a side view of the pivotal connection structure shown in FIG. 10.

FIG. 10 is a perspective view of pivotal connection structure 1012 which is used in another embodiment of the invention. FIGS. 11 and 12 are front and side views of pivotal connection structure 1012.

Similar to pivotal connection structure 112, pivotal connection structure 1012 comprises first member 1033 which connects to connecting member 104 (not shown) and second member 1034 which connects to tube end 124 (not shown). Pivotal connection structure 1012 comprises conduit projections 1042a and 1042b on peripheral sides that on proximal ends communicate with reservoir 110 of tube unit 105 through slot 132 and on distal ends communicate with funnel shaped projections 121a and 121b disposed on the proximal side of connecting member 104.

First member 1033 has first joint portion 1035 and second member 1034 has second joint portion 1036. Pivotal connection structure 1012 further includes joint member 1037 for joining, in a hinged manner, first joint portion 1035 of first member 1033 with second joint portion 1036 of second member 1034. Joint member 1037 (as a whole) has an elongated shape such that it constitutes hinge axis 1038 disposed between first joint portion 1035 and second joint portion 1036 of first member 1033 and second member 1034. In this embodiment, hinge axis 1038 coincides with perpendicular pivot axis 1023.

Compared with pivotal connection structure 112, each of first joint portion 1035 and second joint portion 1036 has a different shape and structure from that of first joint portion 135 and second joint portion 136. More specifically, each of first joint element 1035 and second joint portion 1036 includes base member 1076 having a triangular prism shape, and elastic plate member 1077 extending from base member 1076. In addition, first member 1033 has notch portion 1078 where distal end of elastic plate member 1077 is connected. Base member 1076 is joined to second joint portion 1036 of second member 1034. Elastic plate member 1077 is formed from a resilient material such as those used for joint member 1037. In the embodiment shown in FIG. 10, elastic plate member 1077 is a leaf spring formed by a metal material (e.g., a stainless-steel material).

Pivotal connection structure 1012 works in a similar manner to pivotal connection structure 112 due to the resilient nature of joint member 1037 (i.e., first joint portion 1035 and second joint portion 1036). Thus, pivotal connection structure 1012 is constructed such that joint member 1037 has hinge axis 1038 disposed between first joint portion 1035 of first member 1033 and second joint portion 1036 of second member 1034, which operates as perpendicular pivot axis 1023. Applicator unit 102 can be biased by a return force when pivoted about perpendicular pivot axis 123 away from rest position RP.

Before assembling pivotal connection structure 1012, each of first joint portion 1035 and second joint portion 1036 is prepared independently from the assembling process of pivotal connection structure 1012. Accordingly, the resilience property of first joint portion 1035 and second joint portion 1036 can be controlled easily (compared with, for example, pivotal connection structure 112 which is formed by an injection molding process of a thermoplastic material).

In addition, since pivotal connection structure 1012 for a pivotal movement about perpendicular pivot axis 123 can be formed by a simple structure, the safety syringe extension adapter 1000 can be produced by a simple manufacturing process.

Figure 13:
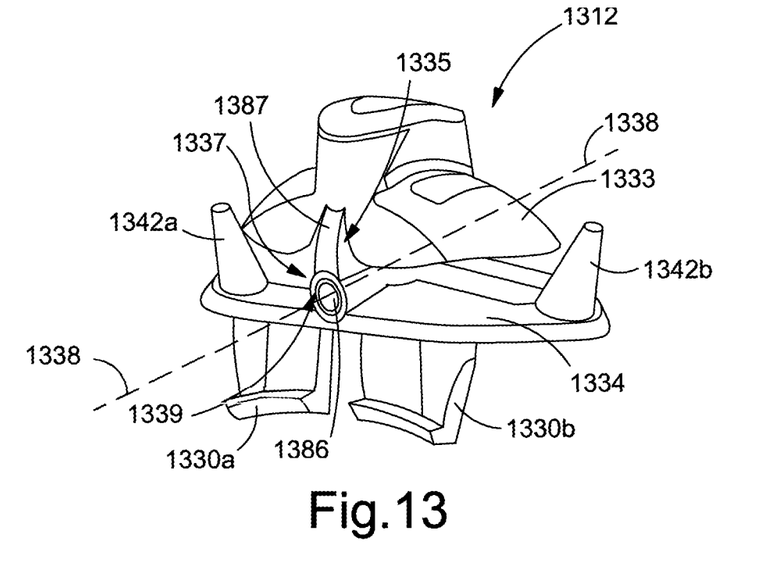
FIG. 13 a perspective view of a pivotal connection structure according to one embodiment of the invention.
Figures 14, 15:
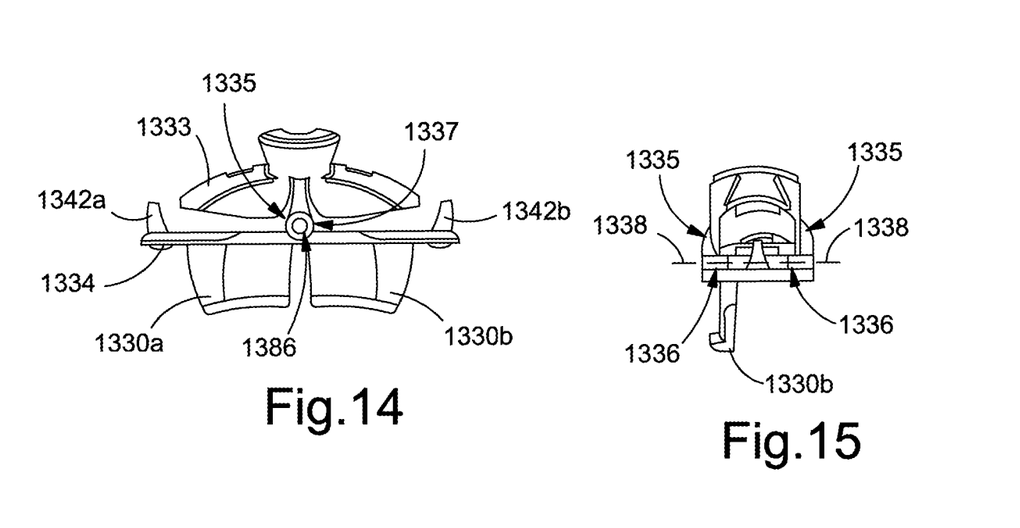
FIG. 14 is a front view of the pivotal connection structure shown in FIG. 13.
FIG. 15 is a side view of the pivotal connection structure shown in FIG. 13.

FIG. 13 is a perspective view of pivotal connection structure 1312 which is used in another embodiment of the invention. FIGS. 14 and 15 are front and side views of pivotal connection structure 1312. Similar to pivotal connection structure 112, pivotal connection structure 1312 comprises first member 1333 which connects to connecting member 104 (not shown) and second member 1334 which connects to tube end 124 (not shown). Pivotal connection structure 1312 comprises conduit projections 1342a and 1342b on peripheral sides that on proximal ends communicate with reservoir 110 of tube unit 105 through slot 132 and on distal ends communicate with funnel shaped projections 121a and 121b disposed on the proximal end of connecting member 104. First member 1333 comprises first joint portion 1335 and second member 1334 comprises second joint portion 1336. Pivotal connection structure 1312 further comprises joint member 1337 for joining, in a hinged manner, first joint portion 1335 of first member 1333 with second joint portion 1336 of second member 1334. Joint member 1337 (as a whole) has an elongated shape such that it constitutes hinge axis 1338 disposed between first joint portion 1335 and second joint portion 1036 of first member 1333 and second member 1334.

Compared with pivotal connection structure 112, each of first joint portion 1335 and second joint portion 1336 has a different shape and structure. More specifically, each of first joint portion 1335 and second joint portion 1336 includes bearing 1386 having a cylindrical shape fixed to second member 1334, and a pivot shaft 1387 having one end fixed to first member 1333 and the other end inserted into bearing 1386. In each of first joint portion 1335 and second joint portion 1336, pivot shaft 1387 can pivot within bearing 1386.

Thus, pivotal connection structure 1312 is constructed such that joint member 1337 has hinge axis 1338 disposed between first joint portion 1335 and second joint portion 1336 of first member 1333 and second member 1334, which operates as perpendicular pivot axis 1323.

Figure 16:
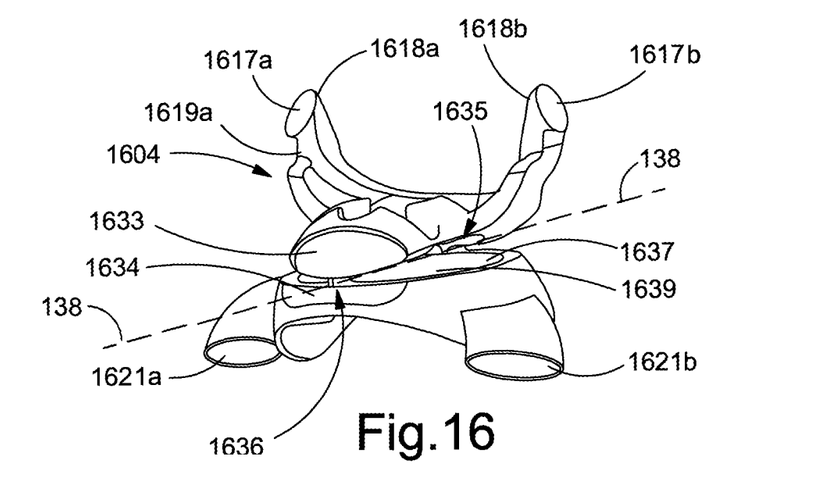
FIG. 16 is a perspective view of the connecting member and pivotal connection structure in one embodiment of the invention.
Figure 17:
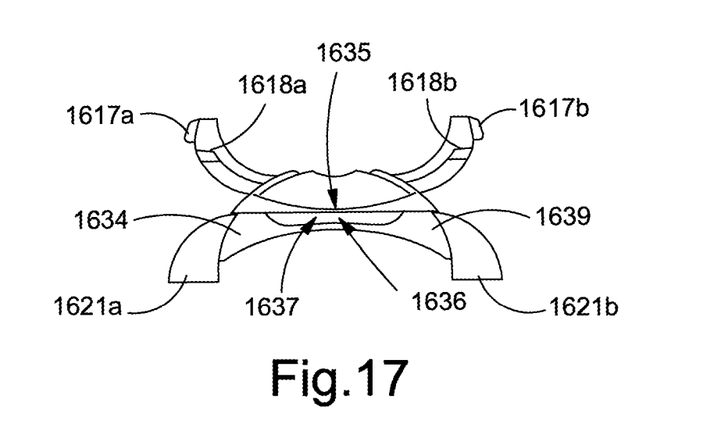
FIG. 17 is a front view of the connecting member and pivotal connection structure shown in FIG. 16.
Figure 18:
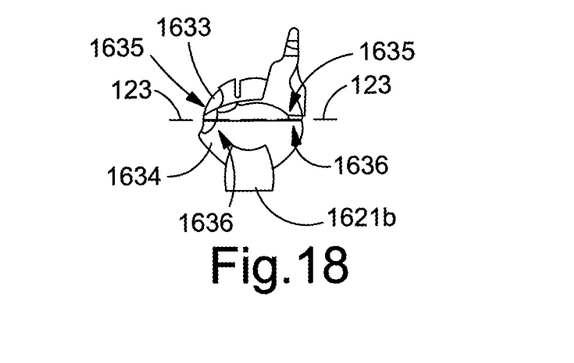
FIG. 18 is a side view of the connecting member and pivotal connection structure shown in FIG. 16.

FIG. 16 is a perspective view and FIGS. 17 and 18 are front and side views of connecting member 1604 and pivotal connection structure 1612 according to one embodiment of the safety syringe extender adapter 100. Referring to FIGS. 16-18, connecting member 1604 comprises first member 1633 which is connected to applicator unit 102; second member 1634 which is connected to tube unit 105; and joint member 1637 for joining, in a hinged manner, first member 1633 with second member 1634. Joint member 1637 has an elongated shape such that it constitutes hinge axis 138 between first member 1633 and second member 1634. Pivotal connection structure 1612 (not shown) comprises conduit projections 1642a and 1642b (not shown) on peripheral sides that on proximal ends communicate with reservoir 1610 of tube unit 105 through slot 1632 and on distal ends communicate with funnel shaped projections 1621a and 1621b disposed on the proximal ends of arms 1616a, 1616b.

It should be noted that joint member 1637 works similarly to joint member 1637 shown in FIG. 4 due to the resilient nature of joint member 1637 (i.e., first joint element 1639 and second joint element 1640). Thus, pivotal connection structure 1612 is constructed such that hinge axis 1638 is disposed between first joint portion 1635 of first member 1633 and second joint portion 1636 of second member 1634, which works as perpendicular pivot axis 123. Applicator unit 1602 can be biased by a return force when pivoted about perpendicular pivot axis 123 away from rest position RP.

In the embodiment shown in FIG. 17, first member 1633, second member 1634 and joint member 1637 are formed from the same material such as a thermoplastic material (e.g., a polyphenylene-ether (PPE) material) by using an injection molding process. Alternatively, first member 1633, second member 1634 and joint member 1637 can be formed by two or three different materials.

Figure 19:
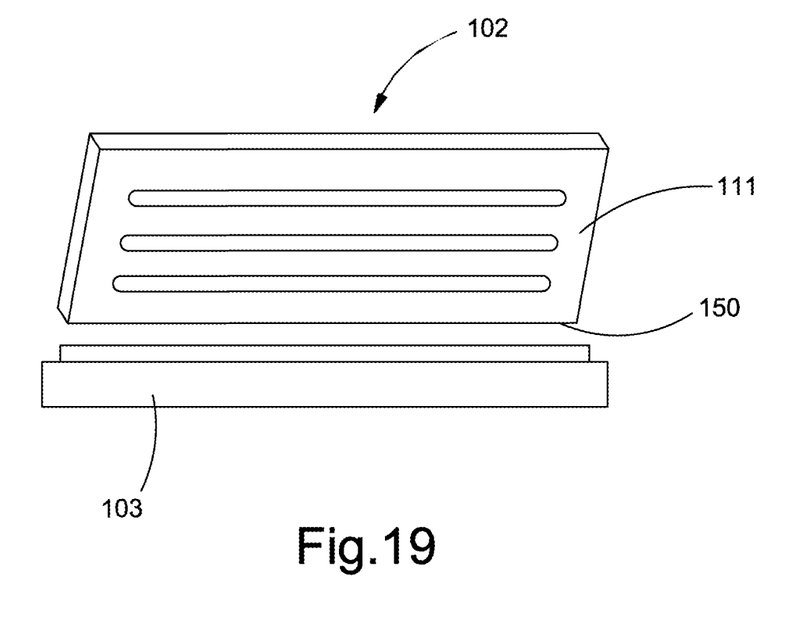
FIG. 19 depicts the wiper guard.

In FIG. 19, one embodiment is shown where wiper guard 1603 is attached to applicator unit 1602 similarly in as wiper guard 1603 is attached to applicator unit 102 in FIGS. 1 and 2. In other embodiments, there is no wiper guard.

In FIG. 19, guide rail 150 is disposed on under surface of applicator unit 102 enabling attachment of wiper guard 103 to applicator unit 102. Wiper guard 103 is made of absorbable materials such as gauze, foam or certain rubbers. A plurality of applicator openings 111 may be disposed on one surface of applicator unit 102 as linear shaped holes or may be formed as slits.

Figure 20A:
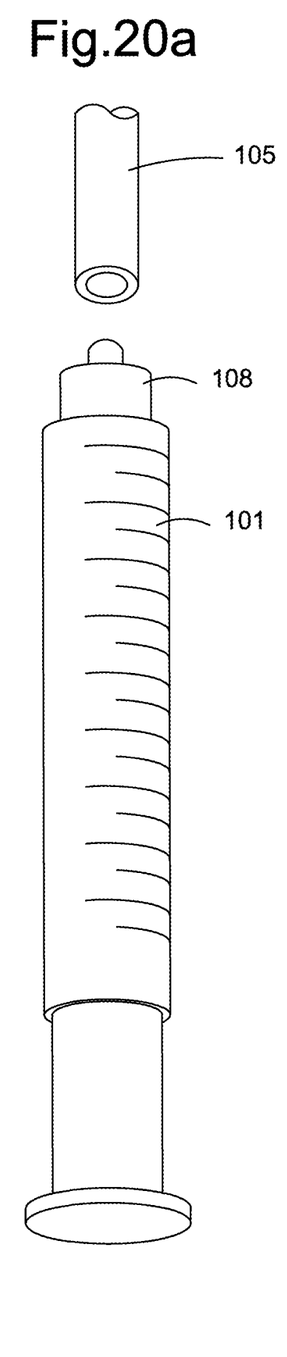
FIGS. 20A, 20B and 20C depict various connections of the tube unit to a syringe.

FIG. 20A depicts connection of tube unit 105 to syringe 2101 with a Luer lock such that a ring-shaped plunger-spring assembly collar 129 on proximal end of tube unit 105 connects into Luer lock threads on syringe 2101 such that fluid can be delivered from syringe 101 through tube reservoir 110 and into safety syringe extension adapter 100 to be deposited on the skin of a patient through applicator openings 111.

Figure 20B:
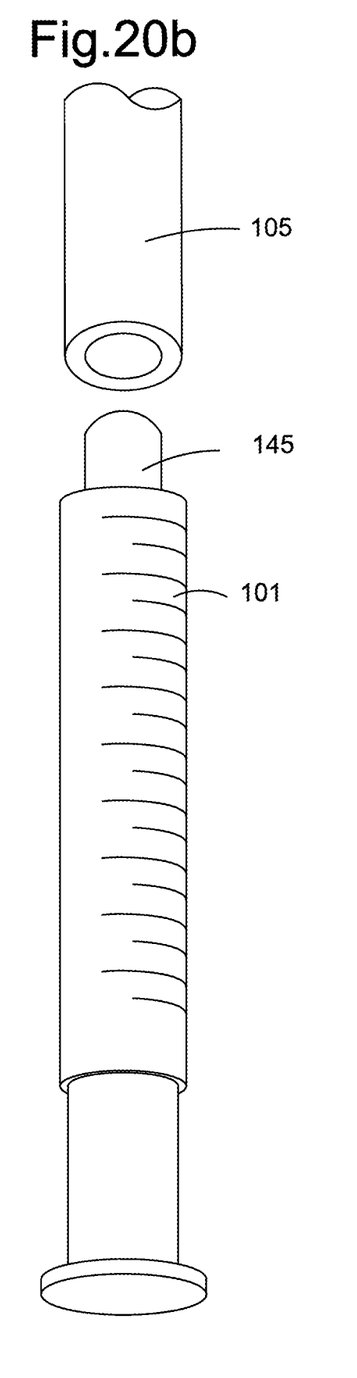

FIG. 20B depicts male configuration 146 of distal end of syringe 101 that mates with female configuration 145 on ring-shaped plunger-spring assembly 129 of proximal end of tube unit 105.

Figure 20C:
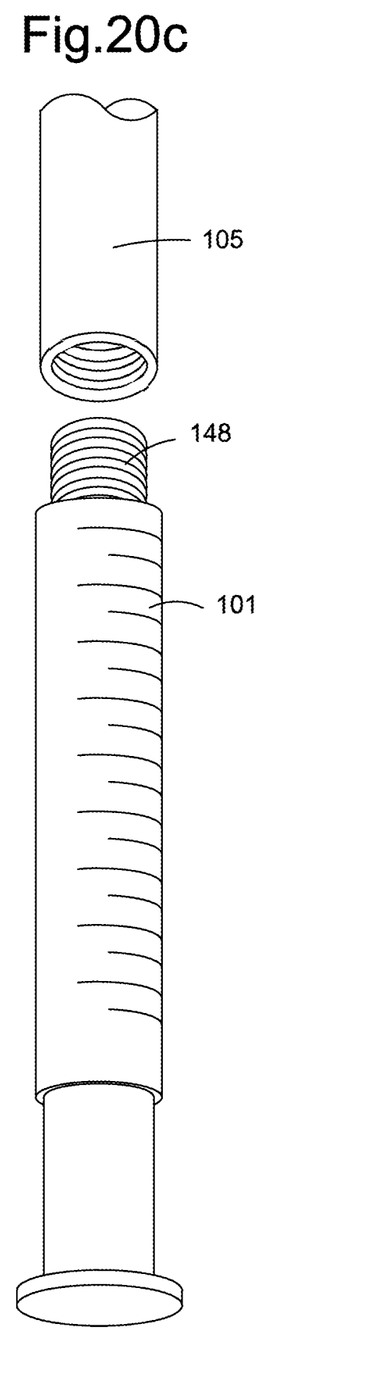

FIG. 20C depicts matching complimentary threads 107 on syringe 101 and threads 148 on tube unit 105 so that these elements may be screwed together.

In operation, fluid is applied to a patient's skin using safety skin adapter extension 100 as follows. Prior to applying fluid to skin, applicator unit 102 is in rest position RP before force is exerted on syringe plunger 149 of syringe 101 in FIG. 1. As a user of the safety syringe extension adapter 100 depresses syringe plunger 149 on syringe 101, fluid contained within syringe 101 is caused to move from syringe 101 into tube reservoir 110 of tube unit 105, then with continued force on plunger 149, fluid is forced distally from tube reservoir 110 through ring-shaped plunger-spring assembly collar 129 and then through pivotal connection structure 112. Specifically, fluid flows through conduit projections 142a, 142b and into funnel shaped projections 121a, 121b in connecting member 104, and thereafter though arms 116a, 116b and inferior to fingers 118a, 118b to openings 119a and 119b respectively of applicator unit 102 into hollow interior of applicator unit 102. Thereafter, fluid flows through applicator openings 111 to enable application of fluid on the skin at the rate determined by the depression of syringe plunger 149. During application of fluid to skin, applicator unit 102 is moved across the skin surface and pivots about parallel pivot axis 113 in response to force applied from the skin and the return force during application of fluid to skin. For example, when applicator unit 102 is biased toward an upright rest position by spring-biased plunger 125, distal end of spring-biased plunger 125 contacts cam surface 114 at a location spaced from parallel pivot axis 113 to impart a biasing force to applicator unit 102. Locating the plunger/cam surface contact point spaced from parallel pivot axis 113 provides leverage so that spring-biased plunger 125 can return applicator unit 102 to its upright, rest position upon load removal. This leverage also enables applicator unit 102 to pivot freely between its upright and fully loaded positions in response to a changing load applied during applying fluid to skin from the user's skin. Additionally, upon application of a force F1, applicator unit 102 leans in direction D1 to reach lean position LP as indicated by moved pivot axis 148. This lean causes a strain at joint member 137 of pivotal connection structure 112. In response to the strain (and due to the resilient nature of joint member 137), joint member 137 of pivotal connection structure 112 generates a reverse force F2 which is applied to first member 133. Reverse force F2 is transmitted to applicator unit 102 through first member 133 as a return force F3 in the direction D2. Return force F3 pushes applicator unit 102 back to rest position RP. Thus, applicator unit 102 pivots about 2 axes (perpendicular and parallel) to conform movement to a user's skin as fluid is applied through applicator openings 111.

The connection of all components, on all embodiments is watertight so that fluid is not lost and is pushed through applicator openings 111 on to the skin and originating from syringe 101. The wiper guard 103 collects and fluid that rolls down inferiorly on skin surface to prevent unintentional spillage of fluid into mucous membranes and areas on skin not intended for fluid.

The various elements may be disposed of in their entirety after one use or the elements made be made of autoclavable materials and plastics and may be reused.

Vials or syringes attached and detached may be made of plastic material, or glass.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A safety syringe extension adapter comprising:
an applicator unit comprising an outer surface defining a hollow interior, a plurality of applicator openings disposed between the hollow interior and the outer surface; a first pivot bearing disposed on one side of the applicator unit having an opening to the hollow interior and a second pivot bearing disposed on the opposite side of the applicator unit from the first pivot bearing having an opening to the hollow interior, and a cam surface disposed on the outer surface;
a connecting member comprising a body, a first hollow arm and a second hollow arm extending at the opposite distal edges of the body, wherein the first hollow arm comprises a first finger at its distal end and the second hollow arm comprises a second finger at its distal end, wherein the first finger comprises an opening at its distal end and the second finger comprises an opening at its distal end, a first funnel projection extending downward from a bottom surface of the connecting member on one end of the connecting member and a second funnel projection extending downward from the bottom surface of the connecting member on the opposite end of the connecting member as the first funnel projection, wherein the first funnel projection is mated with an opening extending through the body of the connecting member which opening is mated also with the first hollow arm and the second funnel projection is mated with an opening extending through the body of the connecting member which opening is mated with the second hollow arm;
a pivotal connection structure comprising a first conduit disposed on one side of a top surface of the pivotal connection structure and a second conduit disposed on the opposite side of the top surface of the pivotal connection structure as the first conduit, wherein each of the first conduit and the second conduit are mated with openings extending from the top surface of the pivotal connection structure to a bottom surface of the pivotal connection structure, a first member disposed on the top surface of the pivotal connection structure and a second member disposed on the bottom surface of the pivotal connection structure, a joint member for joining, in a hinged manner, the first member with the second member, wherein the first member and second member are movable about a hinge pivot axis that passes through the joint member, a first latch arm and a second latch arm extending downward from the bottom surface of the pivotal connection structure, a slot that extends through the center of the pivotal connection structure,
a tube unit comprising an outer tube casing, an inner tube reservoir, a spring-biased plunger placed over a spring that is disposed in the inner tube reservoir, a ring-shaped plunger-spring assembly collar disposed on a bottom end of the tube unit, and a slot on a top end of the tube unit,
wherein the first finger is detachably attached to the first pivot bearing and the second finger is detachably attached to the second pivot bearing thus releasably connecting the connecting member to the applicator unit and allowing applicator unit to pivot about a first pivot axis disposed substantially parallel to an imaginary line between the first pivot bearing and the second pivot bearing,
wherein the first conduit of the pivotal connection structure is inserted into the first funnel projection of the connecting member and the second conduit of the pivotal connection structure is inserted into the second funnel projection of the connecting member, thus detachably connecting the pivotal connection structure and the connecting member,
wherein the first latch arm and the second latch arm are inserted into the slot of the tube unit thus detachably connecting the pivotal connection structure and the tube unit,
wherein the spring-biased plunger is inserted through the slot of the connecting member and contacts the cam surface of the applicator unit,
wherein the pivotal connection structure allows the applicator unit to pivot about the hinge pivot axis in a direction substantially perpendicular to the lateral arrangement of the applicator openings,
wherein the bottom of the tube unit comprises an opening for connection of a syringe, the syringe comprising a hollow interior and a plunger.

2. The safety syringe adapter of claim 1, wherein the syringe is connected to the tube unit via a Luer lock connection.

3. The safety syringe adapter of claim 1, wherein the syringe is connected to the tube unit via threads.

4. The safety syringe adapter of claim 1, wherein the applicator unit further comprises a wiper guard disposed along the first pivot axis.

5. The safety syringe adapter of claim 1, wherein the tube unit, pivotal connection structure and connecting member are disposed along a common longitudinal central axis.

6. The safety syringe adapter of claim 1, wherein the tube unit, pivotal connection structure and connecting member are formed in a single non-separable unit.

7. A safety syringe extension adapter comprising:
an applicator unit comprising an outer surface defining a hollow interior, a plurality of applicator openings disposed between the hollow interior and the outer surface; a first pivot bearing disposed on one side of the applicator unit having an opening to the hollow interior and a second pivot bearing disposed on the opposite side of the applicator unit from the first pivot bearing having an opening to the hollow interior, and a cam surface disposed on the outer surface;
a connecting member comprising a body, a first hollow arm and a second hollow arm extending at the opposite distal edges of the body, wherein the first hollow arm comprises a first finger at its distal end and the second hollow arm comprises a second finger at its distal end, wherein the first finger comprises an opening at its distal end and the second finger comprises an opening at its distal end, a first funnel projection extending downward from a bottom surface of the connecting member on one end of the connecting member and a second funnel projection extending downward from the bottom surface of the connecting member on the opposite end of the connecting member as the first funnel projection, wherein the first funnel projection is mated with an opening extending through the body of the connecting member which opening is mated also with the first hollow arm and the second funnel projection is mated with an opening extending through the body of the connecting member which opening is mated with the second hollow arm;

a pivotal connection structure comprising a first conduit disposed on one side of a top surface of the pivotal connection structure and a second conduit disposed on the opposite side of the top surface of the pivotal connection structure as the first conduit, wherein each of the first conduit and the second conduit are mated with openings extending from the top surface of the pivotal connection structure to a bottom surface of the pivotal connection structure, a first member disposed on the top surface of the pivotal connection structure and a second member disposed on the bottom surface of the pivotal connection structure, a joint member for joining, in a hinged manner, the first member with the second member, wherein the first member and second member are movable about a hinge pivot axis that passes through the joint member, a first latch arm and a second latch arm extending downward from the bottom surface of the pivotal connection structure, a slot that extends through the center of the pivotal connection structure;

a tube unit comprising an outer tube casing, an inner tube reservoir, a spring-biased plunger placed over a spring that is disposed in the inner tube reservoir, a ring-shaped plunger-spring assembly collar disposed on a bottom end of the tube unit, and a slot on a top end of the tube unit; and a syringe comprising a hollow interior and a plunger, wherein the first finger is detachably attached to the first pivot bearing and the second finger is detachably attached to the second pivot bearing thus releasably connecting the connecting member to the applicator unit and allowing applicator unit to pivot about a first pivot axis disposed substantially parallel to an imaginary line between the first pivot bearing and the second pivot bearing, wherein the first conduit of the pivotal connection structure is inserted into the first funnel projection of the connecting member and the second conduit of the pivotal connection structure is inserted into the second funnel projection of the connecting member, thus detachably connecting the pivotal connection structure and the connecting member, wherein the first latch arm and the second latch arm are inserted into the slot of the tube unit thus detachably connecting the pivotal connection structure and the tube unit, wherein the spring-biased plunger is inserted through the slot of the connecting member and contacts the cam surface of the applicator unit, wherein the pivotal connection structure allows the applicator unit to pivot about the hinge pivot axis in a direction substantially perpendicular to the lateral arrangement of the applicator openings.

8. The safety syringe adapter of claim 7, wherein the applicator unit further comprises a wiper guard disposed along the first pivot axis.

9. The safety syringe adapter of claim 7, wherein the tube unit, pivotal connection structure and connecting member are disposed along a common longitudinal central axis.

10. A method of applying a fluid to the skin of a patient, comprising:

filling a syringe with a fluid to be applied to the skin of a patient;

connecting the syringe to the safety syringe adapter of claim 1; and depressing the plunger of the syringe at a rate to be determined by a person who is applying the fluid to the skin of a patient, wherein the fluid passes through the hollow interior of the tube unit, through the first conduit and the second conduit, through the first hollow arm and the second hollow arm, through the openings in the first pivot bearing and the second pivot bearing into the hollow interior of the applicator unit, and through the applicator openings onto the skin of the patient, wherein the applicator unit pivots about the first pivot axis and the hinge pivot axis to conform to the shape of the skin of the patient.

11. A method of applying a fluid to the skin of a patient, comprising:

filling a syringe with a fluid to be applied to the skin of a patient;

connecting the syringe to the safety syringe adapter of claim 7; and depressing the plunger of the syringe at a rate to be determined by a person who is applying the fluid to the skin of a patient, wherein the fluid passes through the hollow interior of the tube unit, through the first conduit and the second conduit, through the first hollow arm and the second hollow arm, through the openings in the first pivot bearing and the second pivot bearing into the hollow interior of the applicator unit, and through the applicator openings onto the skin of the patient, wherein the applicator unit pivots about the first pivot axis and the hinge pivot axis to conform to the shape of the skin of the patient.

* * * * *